US008226612B2

(12) United States Patent  
Nakajima

(10) Patent No.: US 8,226,612 B2
(45) Date of Patent: Jul. 24, 2012

(54) INDWELLING NEEDLE ASSEMBLY

(75) Inventor: Hiroaki Nakajima, Narashino (JP)

(73) Assignee: Medikit Co., Ltd., Tokyo (JP)

( * ) Notice: Subject to any disclaimer, the term of this patent is extended or adjusted under 35 U.S.C. 154(b) by 99 days.

(21) Appl. No.: 11/790,793

(22) Filed: Apr. 27, 2007

(65) Prior Publication Data

US 2007/0255221 A1  Nov. 1, 2007

(30) Foreign Application Priority Data

Apr. 28, 2006  (JP) ................ P2006-124886

(51) Int. Cl.
*A61M 5/178* (2006.01)
(52) U.S. Cl. ......... 604/164.01; 604/164.02; 604/168.01; 604/164.12
(58) Field of Classification Search ............. 604/164.01, 604/164.12, 168.01, 900, 164.02
See application file for complete search history.

(56) References Cited

U.S. PATENT DOCUMENTS

| | | | |
|---|---|---|---|
| 4,654,031 A | 3/1987 | Lentz | |
| 4,747,831 A | 5/1988 | Kulli | |
| 4,813,426 A | 3/1989 | Haber et al. | |
| 4,941,883 A | 7/1990 | Venturini | |
| 5,092,853 A | 3/1992 | Couvertier, II | |
| 5,120,319 A * | 6/1992 | Van Heugten et al. | .. 604/168.01 |
| 5,246,426 A | 9/1993 | Lewis et al. | |
| 5,501,675 A | 3/1996 | Erskine | |
| 5,575,777 A * | 11/1996 | Cover et al. | .................... 604/198 |
| 5,685,855 A | 11/1997 | Erskine | |
| 5,830,190 A | 11/1998 | Howell | |
| 6,077,244 A * | 6/2000 | Botich et al. | .................. 604/110 |
| 6,258,064 B1* | 7/2001 | Smith et al. | ............. 604/164.12 |
| 6,629,956 B1 | 10/2003 | Polidoro et al. | |
| 2005/0240157 A1* | 10/2005 | Amisar et al. | ................ 604/185 |
| 2005/0245875 A1* | 11/2005 | Restelli et al. | ........... 604/164.01 |

FOREIGN PATENT DOCUMENTS

| | | |
|---|---|---|
| EP | 0 730 880 A | 9/1996 |
| EP | 0922466 B | 6/1999 |
| EP | 1 161 962 A | 12/2001 |
| JP | 07-308386 A | 11/1995 |
| JP | 2588375 B | 12/1996 |
| JP | 2647132 B | 5/1997 |
| JP | 10-52499 A | 2/1998 |
| JP | 2910915 B | 4/1999 |
| WO | WO 93/00950 A | 1/1993 |

OTHER PUBLICATIONS

Japanese Patent Office Action for Japanese Patent Application No. 2006-124886, May 31, 2011.

* cited by examiner

*Primary Examiner* — Bhisma Mehta
*Assistant Examiner* — Edelmira Bosques
(74) *Attorney, Agent, or Firm* — Greenblum & Bernstein, P.L.C.

(57) ABSTRACT

A needle assembly for introducing an indwelling catheter into a blood vessel is provided. The needle assembly may include a handle including a flashback chamber configured to allow inflow of flashback blood, and a needle hub. The handle and the needle hub may each be configured with through holes to allow flashback of blood from a needle to the flashback chamber without a mediating member between the through holes.

21 Claims, 9 Drawing Sheets

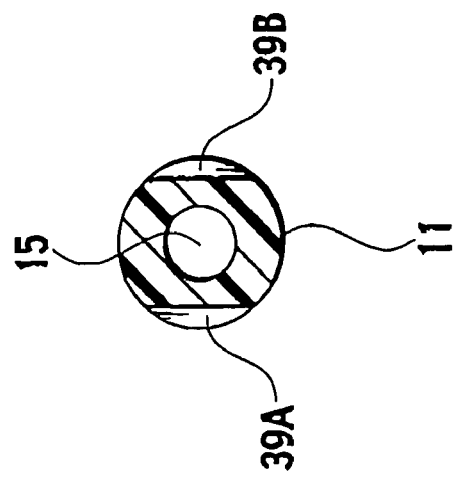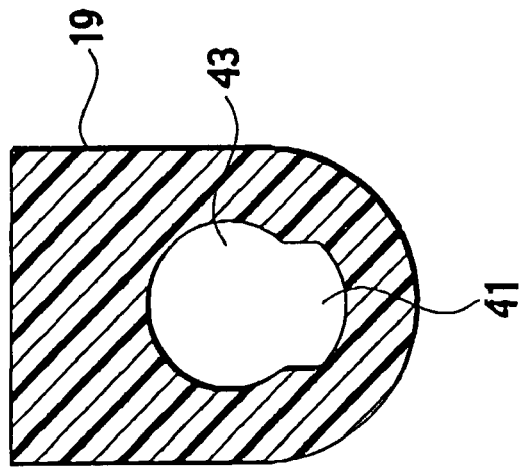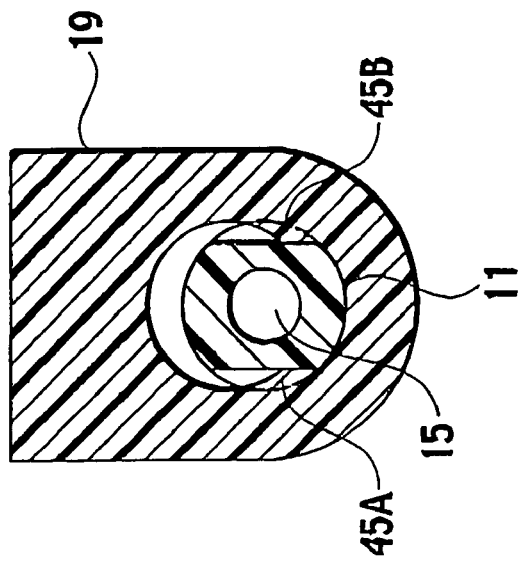

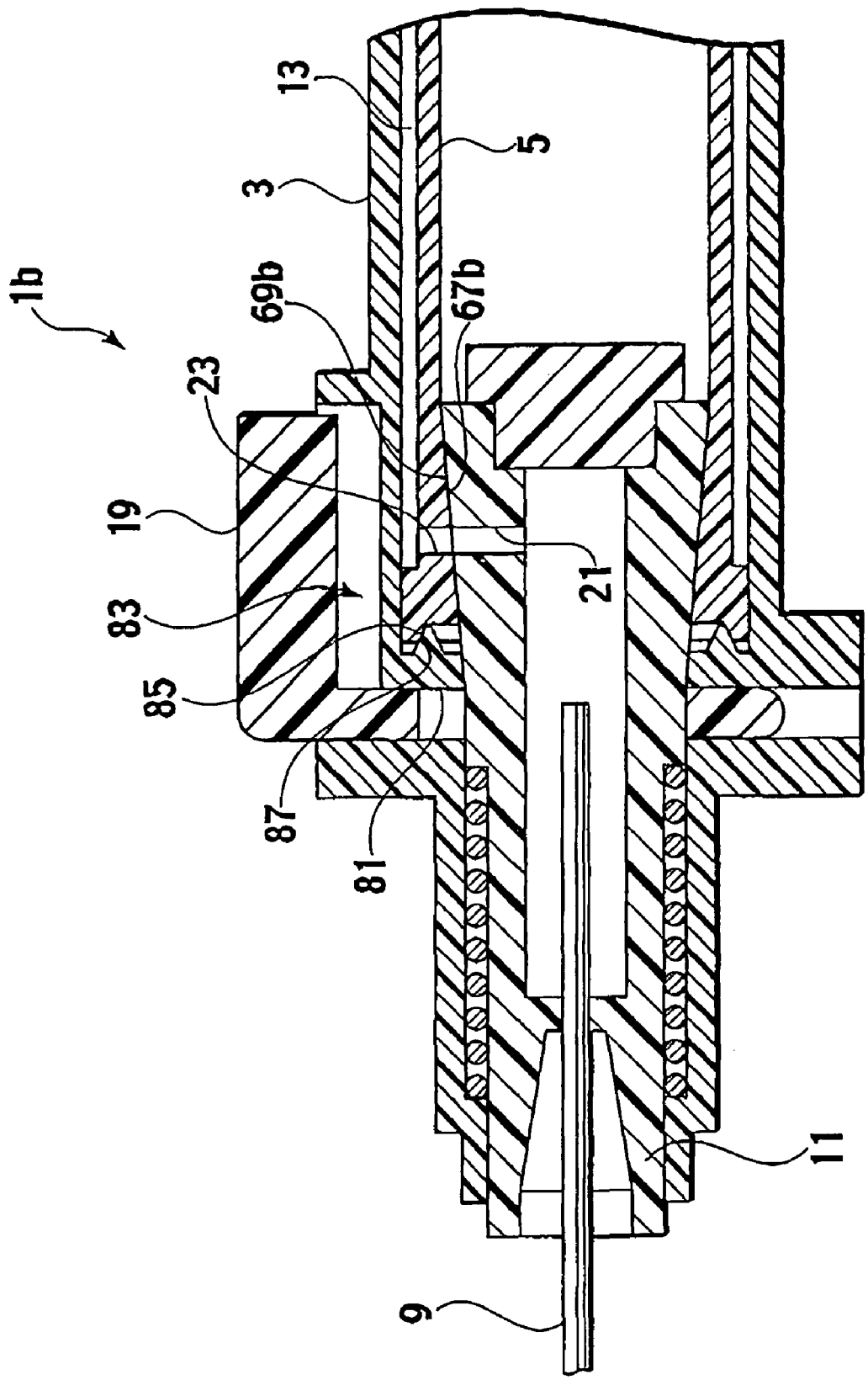

INDWELLING NEEDLE ASSEMBLY

BACKGROUND OF THE INVENTION

1. Field of the Invention

The present invention relates to a needle assembly used for introducing a catheter into a blood vessel of a patient.

2. Description of the Related Art

Catheters are used for administration of various medical fluids to patients. To introduce a catheter into a blood vessel of a patient, a needle assembly with a needle on which the catheter is fitted is frequently used. A medical personnel sticks the needle with the catheter into the patient and then extracts the needle alone. Thereby, the catheter is left indwelled in the blood vessel. In the course of this process, the personnel often lets a small quantity of the patient's blood to flow through the hollow needle to determine whether the needle is properly positioned within the blood vessel or not. This practice of using the blood is termed "flashback".

SUMMARY OF THE INVENTION

The present invention is intended for providing a needle assembly for introducing an indwelling catheter into a blood vessel, which makes a visual check of blood flashback easy.

According to an aspect of the present invention, a needle assembly is used for introducing an indwelling catheter into a blood vessel of a patient. The needle assembly is provided with: a handle having an outer sleeve, an inner sleeve coaxially fixed to the outer sleeve, and a gap between the outer sleeve and the inner sleeve; a hollow needle configured to pierce the patient to guide the catheter into the blood vessel; a needle hub fixed to the needle and movably fit in the handle, which is temporarily retained at a first position where the needle is exposed out of the handle and biased to move toward a second position where the needle retracts in the handle; and a passageway composed of a first through hole penetrating the inner sleeve and a second through hole penetrating the needle hub. These first through hole and the second through hole are so formed as to align with each other to allow flashback of blood from the needle to the gap of the handle without a mediating member between the first through hole and the second through hole only if the needle hub is at the first position.

Preferably, the outer sleeve is made of a translucent material to let the blood in the gap visible from the exterior of the handle.

Preferably, the needle assembly may be further provided with a partition for partitioning the gap into a first portion and a second portion. The partition is interposed between the outer sleeve and the inner sleeve.

Preferably, the needle assembly may be further provided with a release configured to releasably retain the needle hub at the first position. More preferably, the needle hub is provided with a slot and the release is provided with a keyhole opening for releasably latch on the slot. Alternatively more preferably, the needle hub is provided with an axially oblique slot which engages with the release so as to convert a movement of the release into an axial motion of the needle hub toward the second position. Alternatively more preferably, the needle assembly may be further provided with a combination of a rack and a pinion for converting a movement of the release into a motion of the needle hub toward the second position.

Preferably, the needle hub has a flare and the inner sleeve has a tapered internal periphery so that the flare comes in face contact with the tapered internal periphery only if the needle hub is at the first position. More preferably, the first through hole penetrates the flare and the second through hole penetrates the tapered internal periphery.

Preferably, the needle assembly further has a sealing means which has a lip of the inner sleeve and a projection projecting from the outer sleeve to engage with the lip.

According to another aspect of the present invention, a needle assembly is used for introducing an indwelling catheter into a blood vessel of a patient. The needle assembly is provided with: a handle having a flashback chamber visible from an exterior of the handle and a first through hole configured to communicate an interior of the handle with the flashback chamber; a hollow needle configured to pierce the patient to guide the catheter into the blood vessel; a needle hub fixed to the needle and movable in the handle between a first position where the needle is exposed out of the handle and a second position where the needle retracts in the handle, the needle hub having a second through hole so formed as to align with the first through hole of the handle to allow flashback of blood from the needle to the gap of the handle without a mediating member between the first through hole and the second through hole only if the needle hub is at the first position.

Preferably, the handle is at least partly made of a translucent material to let the blood in the flashback chamber visible from an exterior of the handle.

Preferably, the needle assembly may be further provided with a partition for partitioning the flashback chamber into a first portion and a second portion.

Preferably, the needle assembly may be further provided with a release configured to releasably retain the needle hub at the first position. More preferably, the needle hub is provided with a slot and the release is provided with a keyhole opening configured to releasably latch on the slot. Alternatively more preferably, the needle hub is provided with an axially oblique slot engaging with the release so as to convert a movement of the release into an axial motion of the needle hub toward the second position. Alternatively more preferably, the needle assembly is further provided with a combination of a rack and a pinion for converting a movement of the release into a motion of the needle hub toward the second position.

Preferably, the needle hub is provided with a flare and the handle is provided with a tapered internal periphery so that the flare comes in face contact with the tapered internal periphery only if the needle hub is at the first position. More preferably, the first through hole penetrates the flare and the second through hole penetrates the tapered internal periphery.

Preferably, the needle assembly is provided with a sealing combination including a lip of an inner sleeve of the handle and a projection projecting from an outer sleeve of the handle to engage with the lip.

BRIEF DESCRIPTION OF THE DRAWINGS

FIG. 4A is a cross sectional view of the needle assembly, which is taken along a line IV-IV of FIG. 1, and FIGS. 4B and 4C show parts shown in FIG. 4A separately;

FIG. 10 is a partial cross sectional view of a needle assembly in accordance with a third embodiment of the present invention:

DETAIL DESCRIPTION OF THE PREFERRED EMBODIMENT

Embodiments of the present invention will be described hereinafter with reference to FIGS. 1 to 12. Throughout the specification and claims, relative terms "distal" and "proximal" are respectively defined and used as nearest to and remote from a needlepoint of a needle assembly. In FIGS. 1, 5 and 7-12, distal and proximal directions are shown as the left and right directions, respectively. An axis of the needle assembly is indicated by a dashed line in FIG. 1.

First Embodiment

Figure 1:
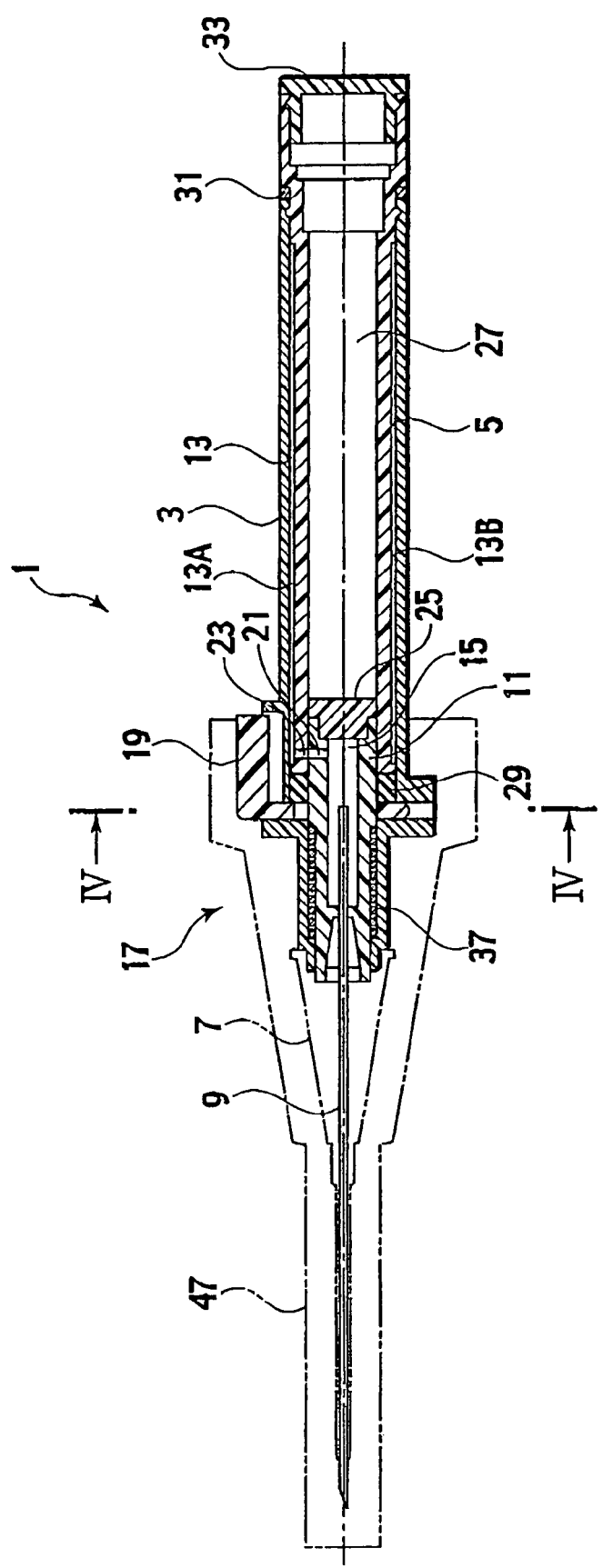
FIG. 1 is a cross sectional view of a needle assembly in accordance with a first embodiment of the present invention.

FIG. 1 shows an initial state, namely before use, of a needle assembly 1 in accordance with a first embodiment of the present invention. The needle assembly 1 is provided with a handle generally composed of an outer sleeve 3 and an inner sleeve 5, a hollow needle 9 on which an indwelling catheter 7 is fitted, and a needle hub 11 to which the needle 9 is fixed, all of which are coaxially aligned. The needle hub 11 is movably fit in the inner sleeve 5.

The outer sleeve 3 coaxially fits on the inner sleeve 5 so as to leave a longitudinally elongated cylindrical gap 13. The gap 13 is so dimensioned as to allow a flow of flashback blood. The gap 13 may be formed sufficiently narrow to spread a small amount of blood over the gap 13 so as to make a visual check from the exterior easy.

The dimensions of the gap 13 may be properly designed in line with the following description. Even if a capacity of the gap 13 is relatively small, flashback of the blood from a blood vessel of a patient via the needle 9 to the gap 13 will occur. However, there may be rare occasions when a sharp end of the needle 9 passes through a blood vessel wall though a medical personnel feels that the needle 9 is properly placed in the blood vessel. Even in these occasions, flashback of blood may temporarily occur but flow of the blood will soon stop. If the capacity is overly small, the personnel will not be able to determine whether the stop is caused by smallness of the capacity or occurrence of passage of the needlepoint through the blood vessel wall. Therefore, the dimensions of the gap 13 are so designed as to have a certain capacity enough to allow such determination. However, as an overly large capacity may cause that the personnel needs a considerable amount of blood flashback, an overly large capacity should be avoided.

Figure 2:
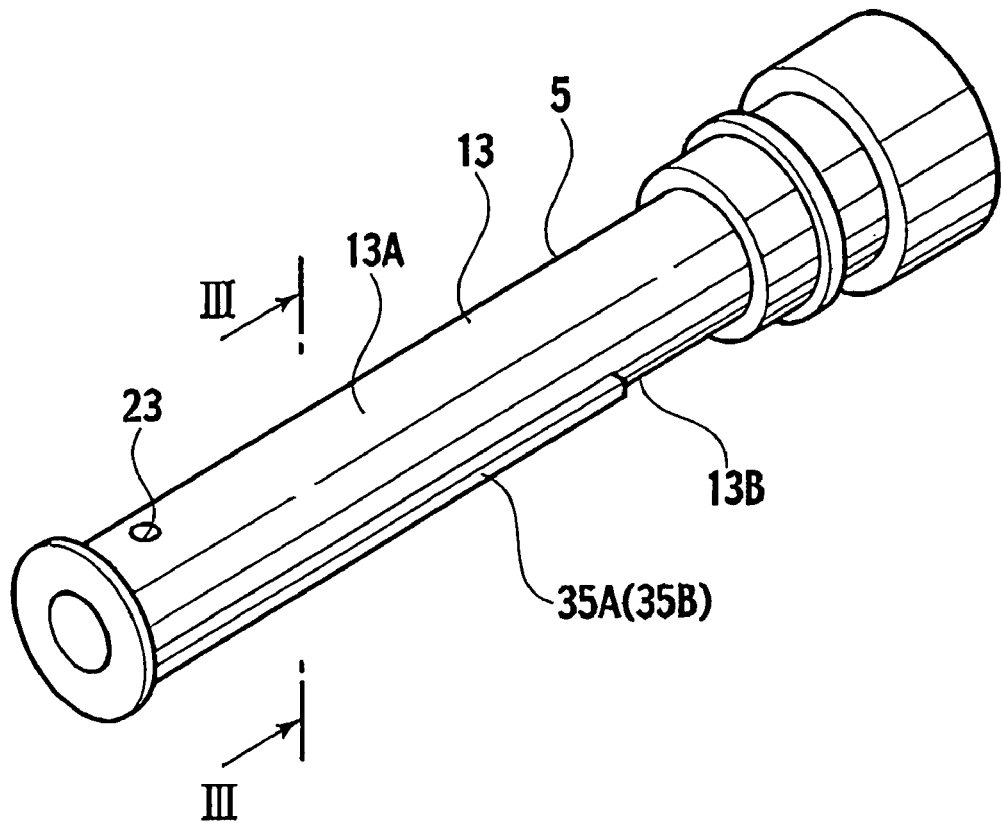
FIG. 2 is a perspective view of an inner sleeve of the needle assembly.

The outer sleeve 3 and the inner sleeve 5 are formed in cylindrical shapes. The outer sleeve 3 is formed generally larger in diameter than the inner sleeve 5. Referring to FIG. 2, the inner sleeve 5 has two outwardly projecting shoulders, outer peripheries of which fit with an inner periphery of the outer sleeve 5. One of the shoulders is at a distal end and another is at a portion close to a proximal end of the inner sleeve 5. The shoulder near the proximal end has a shoulder further larger in diameter on which a proximal end of the outer sleeve 3 is to abut. Dimensions of the outer sleeve 3 and the inner sleeve 5 are such that the outer sleeve 3 coaxially fits on the inner sleeve 5 and the gap 13 therebetween is formed in a longitudinally elongated cylindrical shape. The gap 13 spans both the shoulders of the inner sleeve 3 and is made relatively thin but has a certain capacity. The inner sleeve 3 is further provided with a through hole 23, details of which will be described later.

Intervening between the proximal end of the outer sleeve 3 and the largest shoulder of the inner sleeve 5, a filter 31 is provided to allow escape of air. A cap 33 is fixed to and closes an opening at the proximal end of the inner sleeve 5.

The outer sleeve 3 extends beyond the distal end of the inner sleeve 5 as shown in FIG. 1. At this portion beyond the distal end of the inner sleeve 5, the outer sleeve 3 is provided with a flange portion and a relatively small-in-diameter neck portion.

Figure 5:
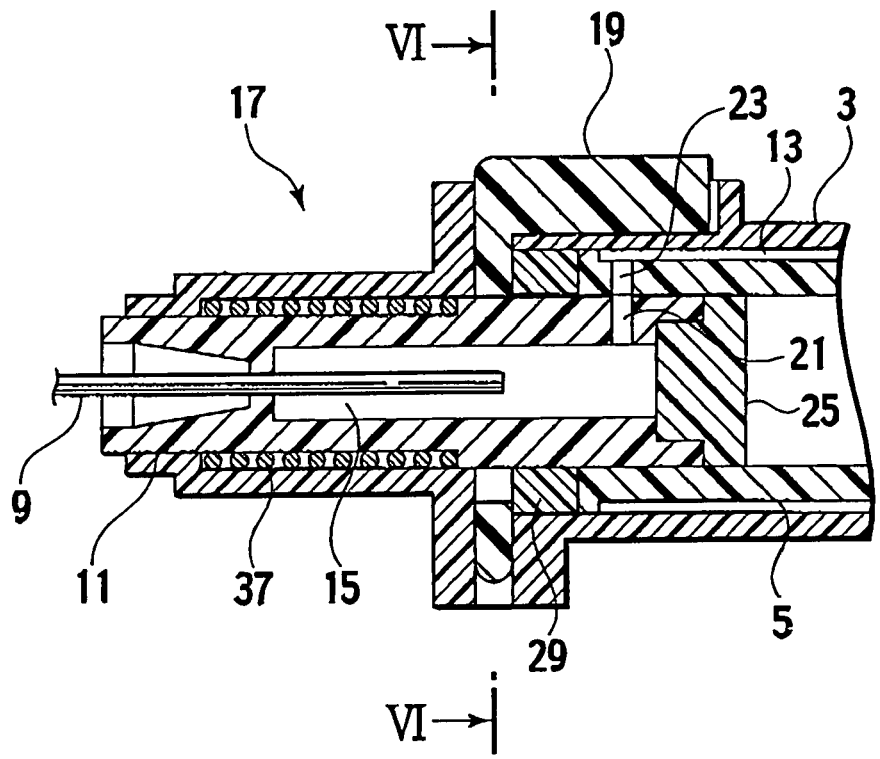
FIG. 5 is a partial cross sectional view of the needle assembly in a condition where a release is pushed down.

Referring to FIG. 5 as well as FIG. 1, the needle hub 11 is generally formed in a relatively short cylindrical shape and so dimensioned as to coaxially slidably fit in the handle. A half of the needle hub 11 near its distal end is formed slightly smaller in diameter to slidably fit in a distal end of the neck portion of the outer sleeve 3. A proximal half is formed slightly larger in diameter to slidably fit in the inner sleeve 5. A step between these halves is to receive a coil spring 37 described later. The interior of the needle hub 11 projects inward to fixingly support the hollow needle 9 and a part of the needle hub 11 near the proximal end is hollowed to form a cavity 15, which communicates with a proximal opened end of the needle 9. The needle hub 11 has a cap 25 tightened on the proximal end, with which the cavity 15 is closed. The needle hub 11 is further provided with a through hole 21 which communicates the cavity 15 with the exterior of the needle hub 11. The through hole 21 is so positioned as to align with the through hole 23 of the inner sleeve 5 when the needle hub 11 is at an initial position. The aligned through holes 21 and 23 come in close contact with each other and form a passageway to allow flow of the flashback blood from needle 9 to the gap 13 of the handle. Formation of the passageway merely requires the close contact between the through holes 21 and 23 but does not require any mediating member such as a duct between the through holes 21 and 23.

The needle assembly 1 is further provided with a bias means 17 for biasing the needle hub 11 to move toward the proximal end of the handle and a release means 19 for releasably retaining the needle hub 11 against force given by the bias means 17. The bias means 17 may be, but not limited to, the coil spring 37 compressed between the neck portion of the outer sleeve 3 and the step of the needle hub 11. The release means 19 is movable in a direction perpendicular to the axis of the needle assembly 1 and has a button-like piece exposed outward such that the medical personnel can manually actuate (push down) the release means 19.

Being interposed among the needle hub 11, the outer sleeve 3, the release means 19 and the distal end of the inner sleeve 5, a circular packing 29 is provided. The packing 29 prevents blood from leaking out through the release means 19.

As such constituted, the needle hub 11 along with the needle 9 is movable in the axial direction in the inner sleeve 5. Length of the needle 9 fixed to the needle hub 11 in total is so related with length of the handle in total that the needle 9 fully retracts in the handle.

Before use, the needle hub 11 is retained at an initial position shown in FIGS. 1 and 5, where the needle 9 is exposed out of the handle. At this initial position, the through holes 21 and 23 are aligned with each other so that the interior of hollow needle 9 spatially communicates with the gap 13 of the handle via the cavity 15 and the through holes 21 and 23 to allow flashback of blood from the hollow needle to the gap of the handle. Therefore, in use, a medical personnel can easily carry out the practice of flashback of blood and also visually check the flashback blood from the exterior of the handle. The release means 19 is made movable in a direction substantially perpendicular to the axial direction and functions as a release button to release the needle hub 11 from this position in accordance with the present embodiment. Therefore, after use, a medical personnel can operate the release means 19 to release and moves the needle hub 11 from the initial position to another position where the needle 9 retracts in the handle.

The outer sleeve 3 is preferably made of a translucent material (more preferably, a translucent resin such as polycarbonate) so that flashback of blood can be visually checked from the exterior of the handle. The inner sleeve 5 and the needle hub 11 may be also made of a translucent material such as polycarbonate or, alternatively, opaquely whitened or colored for higher visibility of the blood thereon.

Figure 3:
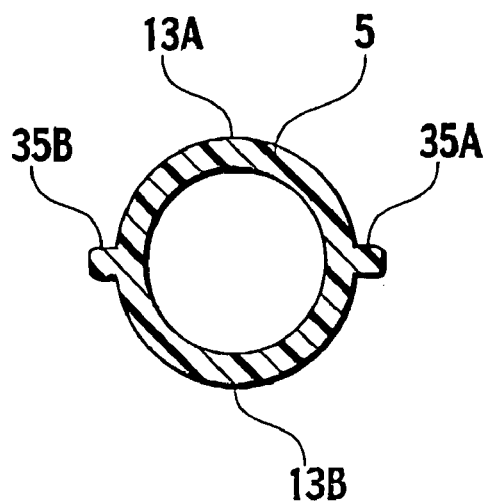
FIG. 3 is a cross sectional view of the inner sleeve, which is taken along a line III-III of FIG. 2.

Referring to FIG. 2 and also FIG. 3, the inner sleeve 5 is further provided with a pair of ribs 35A and 35B radially outwardly projecting from the outer periphery of the inner sleeve 5 and axially extending along the inner sleeve 5. Further, the ribs 35A and 35B are on both sides of the inner sleeve 5 if the through hole 23 is placed upward. The ribs 35A and 35B are to fit in the inner periphery of the outer sleeve 3 and therefore partition the gap 13 into an upper portion 13A and a lower portion 13B. However, these portions 13A and 13B are not completely separated and at least spatially communicate with each other in the vicinity of the proximal end of the gap 13. Instead of the ribs 35A and 35B formed on the inner sleeve 5, ribs radially inwardly projecting on the inner periphery of the outer sleeve 3 may be provided.

As being understood from the above description, the flashback blood flowing through the through holes 21 and 23 first enters in the upper portion 13A of the gap 13 and subsequently spreads toward the proximal end of the gap 13. If a considerable amount of flashback blood enters in the upper portion 13A, such blood may further enter into the lower portion 13B of the gap 13.

Referring to FIGS. 4A-4C, a relationship between the release means 19 and the needle hub 11 will be described hereinafter. The release means 19 has an opening 43, which is composed of an enlarged portion formed of a substantially circular hole to allow the needle hub 11 pass therethrough and a narrowed portion 41 extending opposite to the top as shown in FIG. 4B. The needle hub 11 has a pair of parallel slots 39A and 39B on both sides thereof as shown in FIG. 4C.

Figure 6:
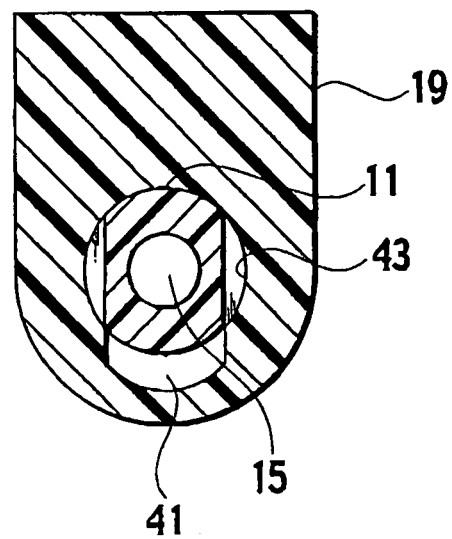
FIG. 6 is a cross sectional view taken along a line VI-VI of FIG. 5.
Figure 7:
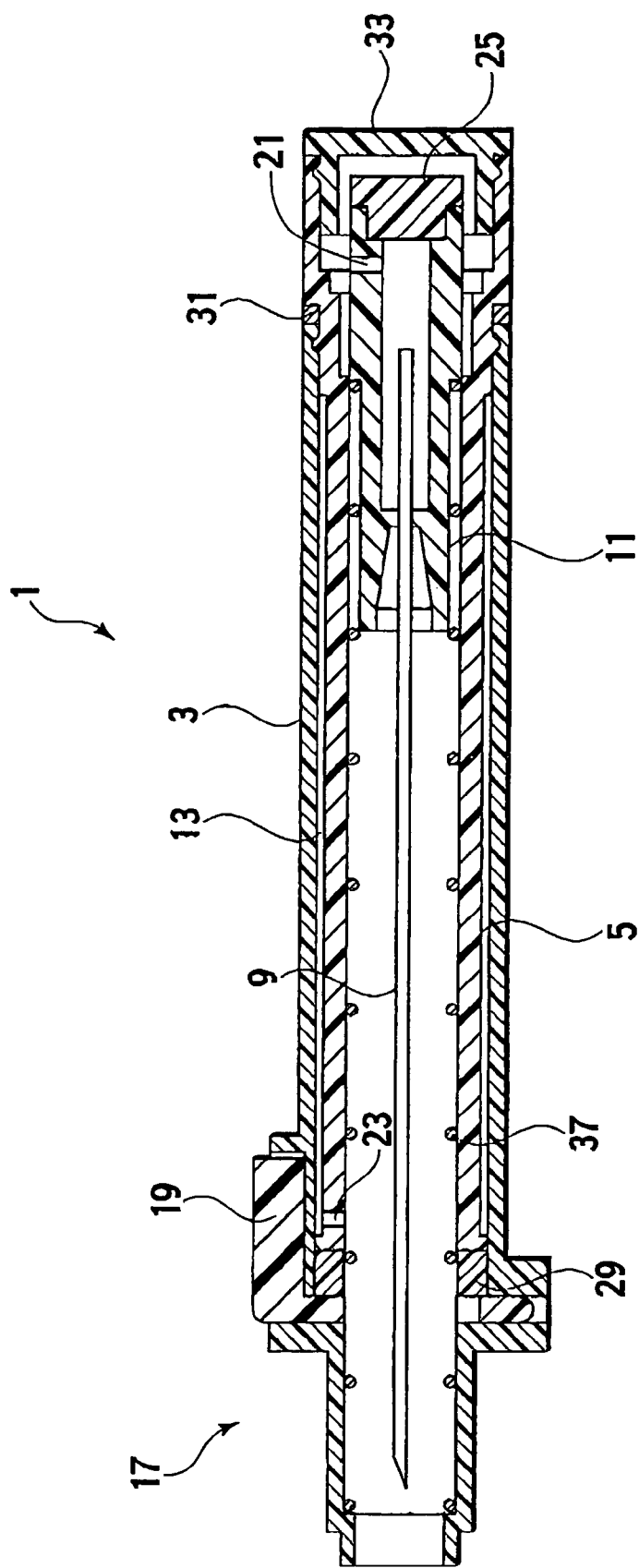
FIG. 7 is a cross sectional view of the needle assembly in a condition where a needle is retracted in a handle.

When the release means 19 is at an initial position (not pushed down), edges of both sides of the narrowed portion 41 latch on the slots 39A and 39B as shown in FIG. 4A. Thereby, the needle hub 11 is retained at the initial position. When the release means 19 is pushed down, the enlarged portion of the opening 43 is made aligned with the needle hub 11 as shown in FIG. 6. Then the needle hub 11 is allowed to move through the aligned opening 43. Subsequently, the bias means 17 moves the needle hub 11 toward the proximal direction. When the needle hub 11 finishes moving to another position where the bias means 17 fully extends or the needle hub 11 abuts on the bottom of the handle, the hollow needle 9 fully retracts in the handle so as to prevent accidental sticking of the needle as shown in FIG. 7.

The needle assembly 1 is supplied with a shield 47, so dimensioned as to fit onto the hollow needle 9 and the release means 19.

A typical method of use of the needle assembly 1 will be described hereinafter.

The method includes removing the shield 47 from the needle assembly 1 to expose the needle 9, and placing the sharp end of the needle 9 on a skin of a patient with aligning the end with a patient's blood vessel. The method further includes inserting the needle 9 along with the catheter 7 through the skin into the blood vessel at a shallow angle so that the sharp end is placed in the blood vessel. The method then includes visually checking blood flashback in the gap 13 through the translucent outer sleeve 3. After confirmation of proper placement of the needle 9 in the blood vessel by the visual check, the method includes advancing the catheter 7 in a distal direction into position in the blood vessel. As proper placement of the catheter is achieved, the method includes pressing down the release means 19 so that the needle hub 11 is release from the initial position and the bias means 17 urges the needle hub 11 into the proximal position where the needle 9 retracts in the handle. Thereby, the needle assembly 1 without the catheter 7 can be disposed of in safety.

Second Embodiment

Figure 8:
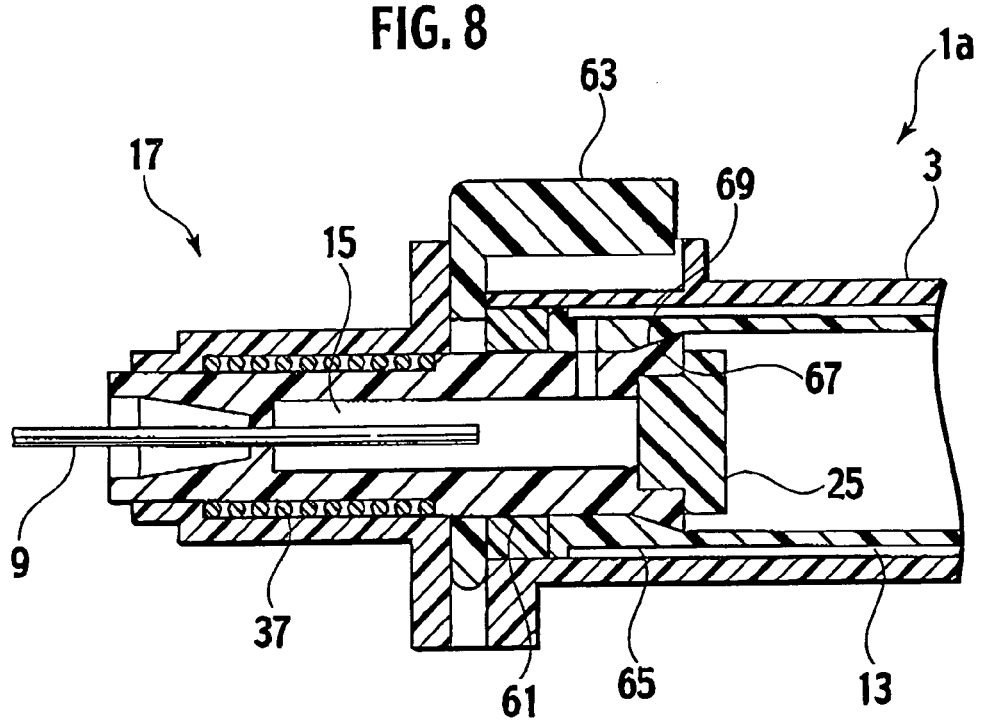
FIG. 8 is a cross sectional view of a needle assembly in accordance with a second embodiment of the present invention.
Figure 9A:
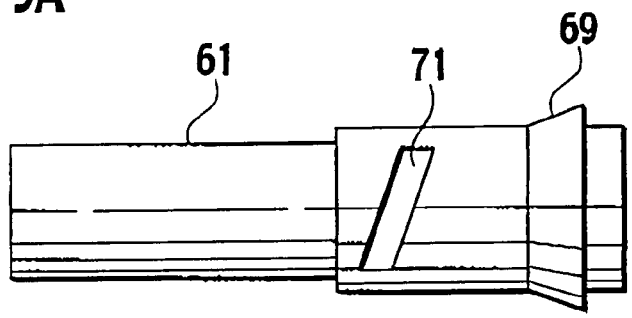
FIG. 9A is an elevational view of a needle hub of the needle assembly.
Figure 9B:
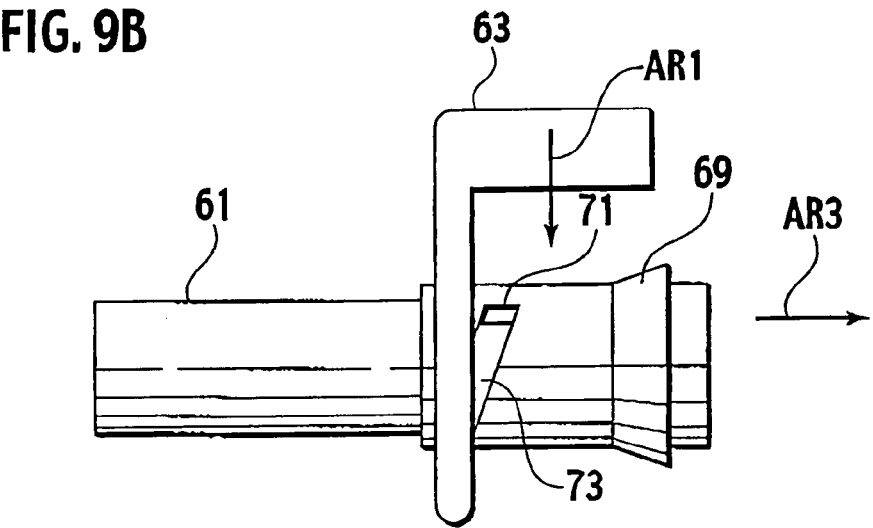
FIG. 9B is an elevational view showing a relationship between the needle hub and a release.

The present invention may be also embodied in a second embodiment as illustrated in FIGS. 8, 9A and 9B. In the following description, substantially the same elements as any of the aforementioned elements are referred with the same reference numerals and detailed descriptions thereof will be omitted or simplified.

A needle assembly 1a in accordance with the second embodiment differs mainly in how and by what the needle hub is retained at the initial position from the needle assembly 1 in accordance with a first embodiment.

Referring to FIG. 8, a needle hub 61 has a flared proximal end portion having a contact face 67. The distal end of the inner sleeve 5 has a tapered internal periphery as a contact face 69 substantially complementary to the contact face 67. These contact faces 67, 69 are brought into face contact with each other by applied force so as to prevent blood from flowing into the inner sleeve 5.

Referring to FIG. 9A, the needle hub 61 has an oblique slot 71 with which a projection 73 of a release means 63 engages. When the release means 63 is pushed down, the projection 73 slides along the slot 71 so as to convert a movement AR1 of the release means 63 in a direction perpendicular to the axis into a motion AR3 of the needle hub 61 in the axial direction. Thereby the contact faces 67, 69 are separated from each other and the needle hub 61 is released from the initial position.

Third Embodiment

The present invention may be also embodied in a third embodiment as illustrated in FIG. 10. In the following description, substantially the same elements as any of the aforementioned elements are referred with the same reference numerals and detailed descriptions thereof will be omitted or simplified.

A needle assembly 1b in accordance with the third embodiment differs mainly in omission of the packing 29 and an instead provided sealing means 83 from the needle assembly in accordance with any of the aforementioned embodiments.

Referring to FIG. 10, the sealing means 83 generally consists of a flared proximal end portion having a contact face 67b of the needle hub, a laterally inwardly throttled lip 81 of the outer sleeve 8, a tapered internal periphery 69b of the inner sleeve 5, a circular edge projecting inward from the lip 81 and the distal end of the inner sleeve 5. Both the lip 81 and the internal periphery 69b are so formed to be in close contact with the contact face 67b so as to prevent leakage of the blood around the passageway formed of the through holes 21 and 23 and through the lip 81. The circular edge of the lip 81 has a conical outer face 87 and the distal end of the inner sleeve 5 has a complementary face 85. These faces 85 and 87 are so formed to be in face contact with each other, thereby leakage of the blood therethrough is prevented.

Fourth Embodiment

Figure 11A:
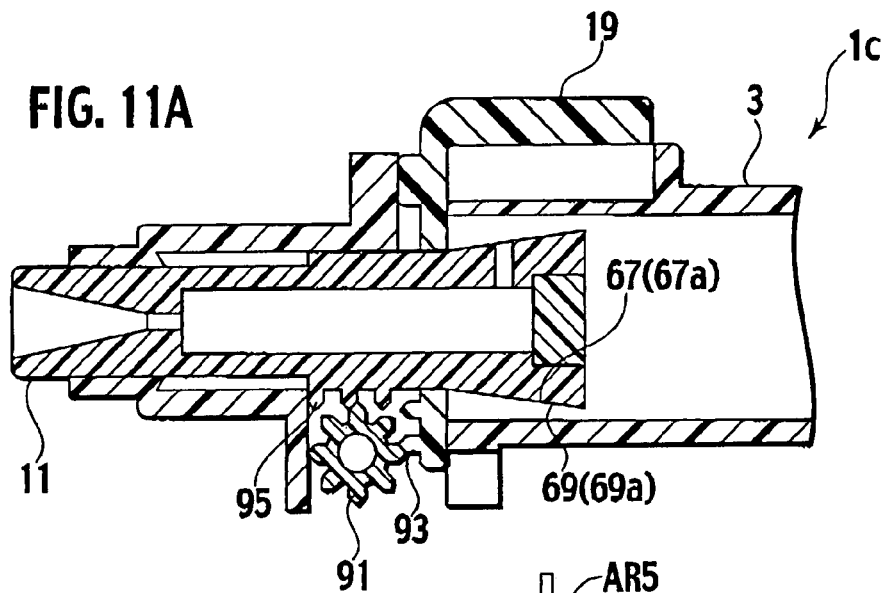
FIGS. 11A-11C are partial cross sectional views of a needle assembly in accordance with a fourth embodiment of the present invention.
Figure 11B:
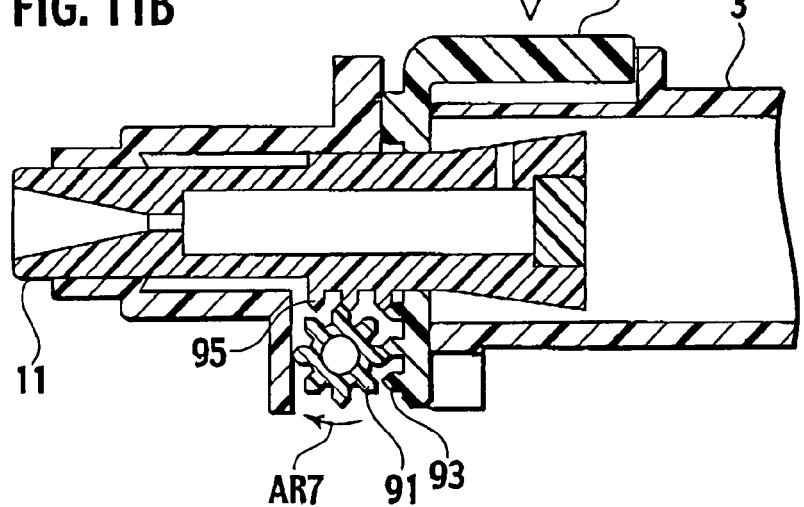
Figure 11C:
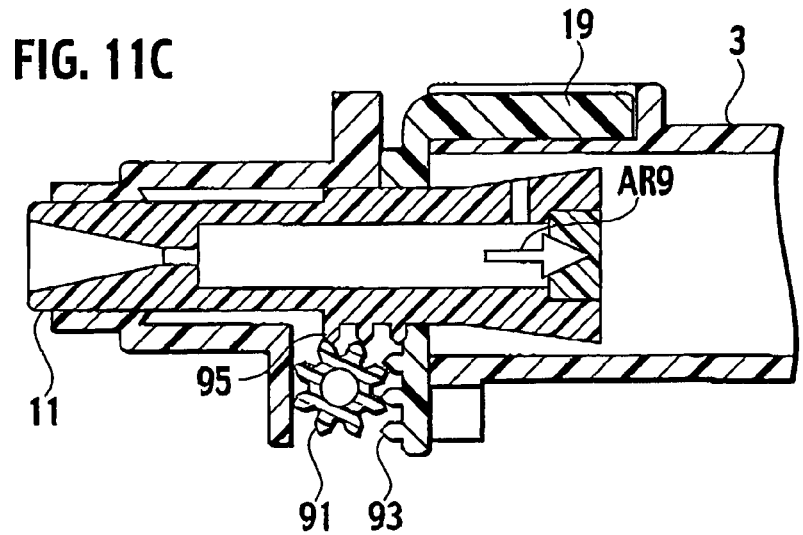

The present invention may be also embodied in a fourth embodiment as illustrated in FIGS. 11A to 11C. In the following description, substantially the same elements as any of the aforementioned elements are referred with the same reference numerals and detailed descriptions thereof will be omitted or simplified.

A needle assembly 1c in accordance with the fourth embodiment differs mainly in that a means for releasably retaining the needle hub 11 includes a combination of racks and a pinion for converting motion of the release means 19 to the needle hub 11 from the needle assembly of any of the above embodiments.

The needle hub 11 has a flared proximal end portion having a contact face 67 (67a). The distal end of the inner sleeve 5 has a tapered internal periphery as a contact face 69 (69a) substantially complementary to the contact face 67 (67a). These contact faces 67 (67a), 69 (69a) are brought into face contact with each other by applied force so as to prevent blood from flowing into the inner sleeve 5.

The release means 19 includes a rack 93 having gear-like teeth in series in a direction where the release means 19 is actuated. The needle hub 11 also includes a rack 95 having gear-like teeth in series along the axial direction. A rotatable pinion 91 is provided so as to engage with both the racks 93 and 95 as shown in FIG. 11A. If the release means 19 is actuated (pushed down), the movement of the rack 93 causes rotation AR7 of the pinion 91 as shown in FIG. 11B and the rotation AR7 further causes motion AR9 of the rack 95 in the axial direction toward the proximal end as shown in FIG. 11C. Thereby, the needle hub 11 is release from the initial position.

Figure 12:
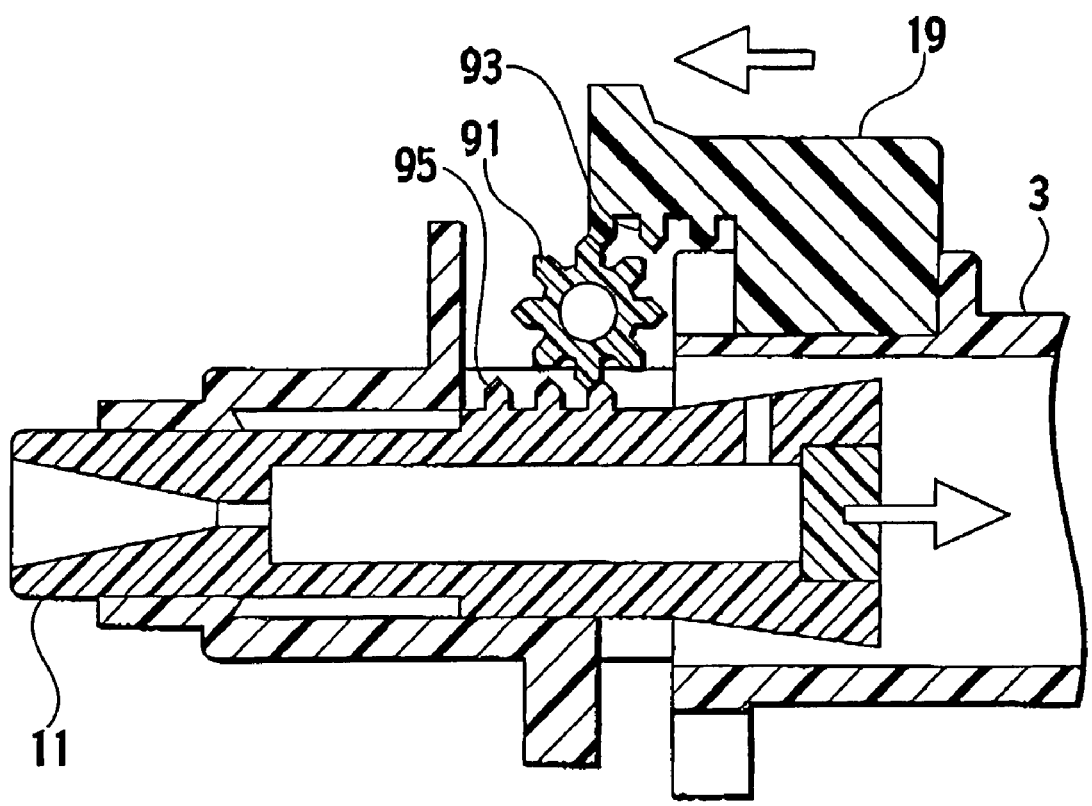
FIG. 12 shows a modification of the fourth embodiment.

Such a rack-and-pinion mechanism may be also embodied as in a version shown in FIG. 12. The release means 19 is made movable in the axial direction and the rack 93 is formed thereon along the axial direction. As being understood from FIG. 12, if the release means 19 is actuated forward, the needle hub 11 moves rearward by means of the combination of the racks 93, 95 and the pinion 91.

Although the invention has been described above by reference to a certain embodiment of the invention, the invention is not limited to the embodiments described above. Modifications and variations of the embodiment described above will occur to those skilled in the art, in light of the above teachings.

The contents of Japanese Patent Application No. 2006-124886 (filed Apr. 28, 2006) are incorporated herein by reference in its entirety.

What is claimed is:

1. A needle assembly of an indwelling catheter for introducing the indwelling catheter into a blood vessel of a patient, the needle assembly comprising:
  a handle including an outer sleeve, an inner sleeve coaxially fixed directly to the outer sleeve, and a flashback chamber configured to allow inflow of flashback blood, the flashback chamber being held between the outer sleeve and the inner sleeve;
  a hollow needle configured to pierce the patient to guide the catheter into the blood vessel;
  a needle hub fixed to the needle and movably fit in the handle, the needle hub being temporarily retained at a first position where the needle is exposed out of the handle and biased to move toward a second position where the needle retracts in the handle; and
  a passageway including a first through hole penetrating the inner sleeve and a second through hole penetrating the needle hub, the first through hole and the second through hole configured to align with and contact each other to allow flashback of blood from the needle to the flashback chamber of the handle without a mediating member between the first through hole and the second through hole when the needle hub is at the first position.

2. The needle assembly of claim 1, wherein the outer sleeve includes a translucent material to let the blood in the flashback chamber be visible from an exterior of the handle.

3. The needle assembly of claim 1, further comprising: a partition for partitioning the flashback chamber into a first portion and a second portion, the partition being interposed between the outer sleeve and the inner sleeve.

4. The needle assembly of claim 1, further comprising: a release configured to releasably retain the needle hub at the first position.

5. The needle assembly of claim 4, wherein the needle hub includes a slot and the release includes a keyhole opening configured to releasably latch on the slot.

6. The needle assembly of claim 4, wherein the needle hub includes an axially oblique slot engaging with the release so as to convert a movement of the release into an axial motion of the needle hub toward the second position.

7. The needle assembly of claim 4, further comprising: a combination of a rack and a pinion for converting a movement of the release into a motion of the needle hub toward the second position.

8. The needle assembly of claim 1, wherein the needle hub includes a flare and the inner sleeve includes a tapered internal periphery so that the flare comes in face contact with the tapered internal periphery only if the needle hub is at the first position.

9. The needle assembly of claim 8, wherein the first through hole penetrates the flare and the second through hole penetrates the tapered internal periphery.

10. The needle assembly of claim 1, further comprising: a sealing combination including a lip of the inner sleeve and a projection projecting from the outer sleeve to engage with the lip.

11. A needle assembly of an indwelling catheter for introducing the indwelling catheter into a blood vessel of a patient, the needle assembly comprising:
  a handle including a flashback chamber visible from an exterior portion of the handle and a first through hole configured to communicate an interior portion of the handle with the flashback chamber, and the interior portion of the handle being coaxially fixed directly to the exterior portion of the handle;
  a hollow needle configured to pierce the patient to guide the catheter into the blood vessel; and
  a needle hub fixed to the needle and movable in the handle between a first position where the needle is exposed out of the handle and a second position where the needle retracts in the handle, the needle hub including a second through hole configured to align with and contact the first through hole of the handle to allow flashback of blood from the needle to the flashback chamber of the handle without a mediating member between the first through hole and the second through hole when the needle hub is at the first position.

12. The needle assembly of claim 11, wherein the handle includes a translucent material to let the blood in the flashback chamber be visible from an exterior of the handle.

13. The needle assembly of claim 11, further comprising: a partition for partitioning the flashback chamber into a first portion and a second portion.

14. The needle assembly of claim 11, further comprising: a release configured to releasably retain the needle hub at the first position.

15. The needle assembly of claim 14, wherein the needle hub includes a slot and the release includes a keyhole opening configured to releasably latch on the slot.

16. The needle assembly of claim 14, wherein the needle hub includes an axially oblique slot engaging with the release so as to convert a movement of the release into an axial motion of the needle hub toward the second position.

17. The needle assembly of claim 14, further comprising: a combination of a rack and a pinion for converting a movement of the release into a motion of the needle hub toward the second position.

18. The needle assembly of claim 11, wherein the needle hub includes a flare and the handle includes a tapered internal periphery so that the flare comes in face contact with the tapered internal periphery only if the needle hub is at the first position.

19. The needle assembly of claim 18, wherein the first through hole penetrates the flare and the second through hole penetrates the tapered internal periphery.

20. The needle assembly of claim 11, further comprising: a sealing combination including a lip of an inner sleeve of the handle and a projection projecting from an outer sleeve of the handle to engage with the lip.

21. A needle assembly of an indwelling catheter for introducing the indwelling catheter into a blood vessel of a patient, the needle assembly comprising:
a handle including an outer sleeve, an inner sleeve coaxially fixed directly to the outer sleeve, the inner sleeve and the outer sleeve provided with at least one of the projected portion and a recessed portion so as to fix the inner sleeve and the outer sleeve each other and a flashback chamber configured to allow inflow of flashback blood, the flashback chamber being held between the outer sleeve and the inner sleeve;
a hollow needle configured to pierce the patient to guide the catheter into the blood vessel; and
a needle hub fixed to the needle and movably fit in the handle, the needle hub being temporarily retained at a first position where the needle is exposed out of the handle and biased to move toward a second position where the needle retracts in the handle; and
a passageway including a first through hole penetrating the inner sleeve and a second through hole penetrating the needle hub, the first through hole and the second through hole being configured to align with and contact each other to allow flashback of blood from the needle to the flashback chamber of the handle without a mediating member between the first through hole and the second through hole when the needle hub is at the first position.

* * * * *

UNITED STATES PATENT AND TRADEMARK OFFICE
CERTIFICATE OF CORRECTION

| | | |
|---|---|---|
| PATENT NO. | : 8,226,612 B2 | |
| APPLICATION NO. | : 11/790793 | |
| DATED | : July 24, 2012 | |
| INVENTOR(S) | : H. Nakajima | |

It is certified that error appears in the above-identified patent and that said Letters Patent is hereby corrected as shown below:

At column 10, line 12 (claim 21, line 8), please change "outer sleeve each other" to -- outer sleeve to each other --.

Signed and Sealed this
Twelfth Day of March, 2013

Teresa Stanek Rea
*Acting Director of the United States Patent and Trademark Office*